United States Patent [19]
Baker, Jr.

[11] Patent Number: 5,205,285
[45] Date of Patent: Apr. 27, 1993

[54] VOICE SUPPRESSION OF VAGAL STIMULATION

[75] Inventor: Ross G. Baker, Jr., Houston, Tex.

[73] Assignee: Cyberonics, Inc., Webster, Tex.

[21] Appl. No.: 715,428

[22] Filed: Jun. 14, 1991

[51] Int. Cl.⁵ .............................................. A61N 1/08
[52] U.S. Cl. ........................ 128/423 R; 128/419 R; 128/419 C
[58] Field of Search ............ 128/419 R, 419 C, 420.5, 128/420.6, 423 R

[56] References Cited

U.S. PATENT DOCUMENTS 4,791,931 12/1988 Slate .............................. 128/419 PG
5,111,814 5/1992 Goldfarb ......................... 128/419 R Primary Examiner—Kyle L. Howell
Assistant Examiner—Scott M. Getzow
Attorney, Agent, or Firm—Leitner, Greene & Christensen

[57] ABSTRACT

In conjunction with a medical device for stimulating the vagus nerve of a patient to modulate the electrical activity thereof as part of a prescribed therapy, apparatus is provided to selectively suppress the stimulation while the patient is speaking, to avoid undesirable modulation of the voice. The suppression apparatus includes a speech sensor and discriminator, to detect speech by the patient while avoiding false detection attributable to sounds other than speech. The suppression of nerve stimulation is ceased after a preset time interval regardless of continued detection of speech, to assure that beneficial therapy is not unduly inhibited in favor of mere cosmetic considerations or in the presence of prolonged false detections. In the preferred embodiment, the discriminator selectively varies the sensitivity of the suppression apparatus to speech by the patient to enhance its selectivity over sounds attributable to other sources, such as by changing the value of a threshold level which must be crossed before the suppression of nerve stimulation can occur or continue, and by filtering out disturbances.

20 Claims, 2 Drawing Sheets

VOICE SUPPRESSION OF VAGAL STIMULATION

BACKGROUND OF THE INVENTION

The present invention relates generally to techniques for stimulation of the vagus nerve, and more particularly to methods and apparatus for suppressing or inhibiting stimulation of the vagus nerve while the individual undergoing the stimulation is speaking.

Neural stimulating devices (neurostimulators) for generating and applying electrical impulses to the vagus nerve of an epileptic patient to modulate the electrical activity of the nerve(s) as part of a prescribed therapy are currently undergoing clinical testing and investigation. A side effect of such vagal stimulation in at least some patients is the presence of a noticeable modulation of the patient's voice when he or she speaks during actual application of the stimulating signals to the nerve.

It is a principal object of the present invention to provide techniques for avoiding undesirable voice modulation of patients undergoing vagal stimulation therapy.

However, the desire to eliminate an objectionable or annoying modulation of the patient's voice, which is essentially a cosmetic consideration, must be balanced against the need to assure that the appropriate therapy will be delivered.

Accordingly, it is another object of the invention to avoid, to a reasonable extent, undesirable voice modulation of patients undergoing vagal stimulation therapy, while maintaining a bias in certain circumstances toward ongoing delivery of the therapy as prescribed.

SUMMARY OF THE INVENTION

In essence, in conjunction with a medical device for stimulating the vagus nerve of a patient to modulate the electrical activity thereof as part of a prescribed therapy, the present invention provides sensing means to detect the patient's speech and to halt or delay the vagal stimulation during at least a part of the time that speech continues to be detected. The result is selective suppression of the stimulation while the patient is speaking. The sensing means includes detection and discrimination apparatus, to detect speech by the patient while avoiding false detection attributable to sounds from other sources.

In a presently preferred embodiment, the suppression of nerve stimulation ceases after a preset time interval regardless of continued detection of speech, to assure that beneficial therapy is not unduly inhibited in favor of mere cosmetic considerations or in the presence of prolonged false detections. The discriminator selectively varies the sensitivity of the suppression apparatus to the patient's voice while enhancing selectivity over other sounds in the vicinity, for example by changing the value of a threshold level which must be crossed before the suppression of nerve stimulation can occur or continue, and filtering out disturbances.

Although a number of techniques exist by which speech may be detected, such as by sensing myopotentials from muscles involved in speech, or neural potentials, or impedance changes in the tissues involved in speech, for example, the preferred embodiment of the present invention employs a vibration transducer, such as a piezoelectric polymer converter, preferably a plastic material commercially available under the trademark Kynar (of Pennwalt Company). Alternatively, a piezoelectric crystal converter may be used as the vibration transducer. The transducer detects vibrations caused by speech-generated sound and converts them to a corresponding electrical signal. It may be located near the vocal tract, or, preferably, for reasons of greater protection and ease of implantation, within the case (housing) of the implantable microprocessor-based stimulus generator which delivers the programmed therapy to the patient.

Although it possesses some clear advantages over other techniques for voice or speech detection such as those mentioned above, principally in avoidance of surgical complexities of implantation, a vibration sensor alone is not highly selective of speech-generated sounds or frequencies. However, that shortcoming is readily overcome by appropriate signal enhancement. For example, the system may be designed with programmable or adaptive sensitivities to the signal derived from the speech-generated vibrations. To improve discrimination, selective filtering is performed in the known voice frequency band of from about 300 to about 3,000 Hertz (Hz). Further noise immunity may be provided by varying the detection threshold(s) according to the background noise present.

Therefore, it is another broad object of the present invention to provide improved methods and apparatus for medical therapy through stimulation of the vagus nerve.

A more specific object is to provide a method and apparatus for vagal neurostimulation which includes selectively suppressing or inhibiting stimulation when the patient is speaking, and avoiding such suppression in the presence of false signals or after prolonged speaking, in favor of delivery of the stimulation therapy.

BRIEF DESCRIPTION OF THE DRAWINGS

The above and still further objects, features and attendant advantages of the invention will become apparent from a consideration of the following detailed description of the preferred embodiments thereof, taken in conjunction with the accompanying drawings, in which.

DETAILED DESCRIPTION OF THE PREFERRED EMBODIMENT AND METHOD

Figure 1:
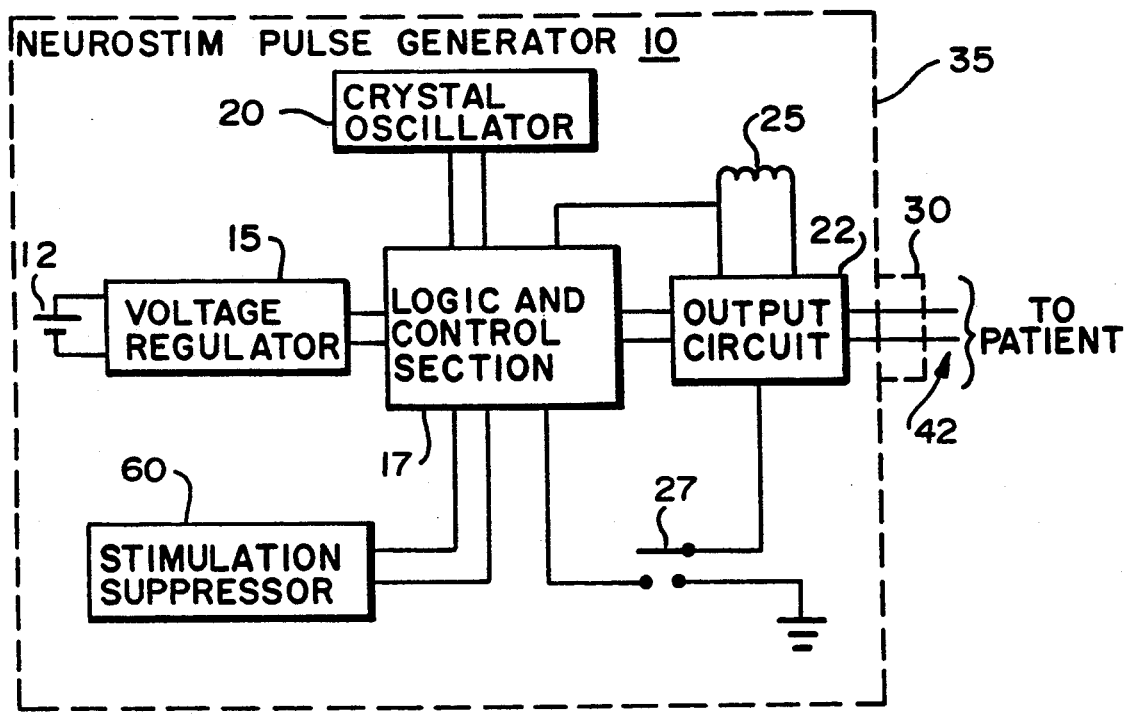
FIG. 1 is a simplified block diagram of an exemplary implantable neurostimulator to which the principles of the present invention may be applied.
Figure 2:
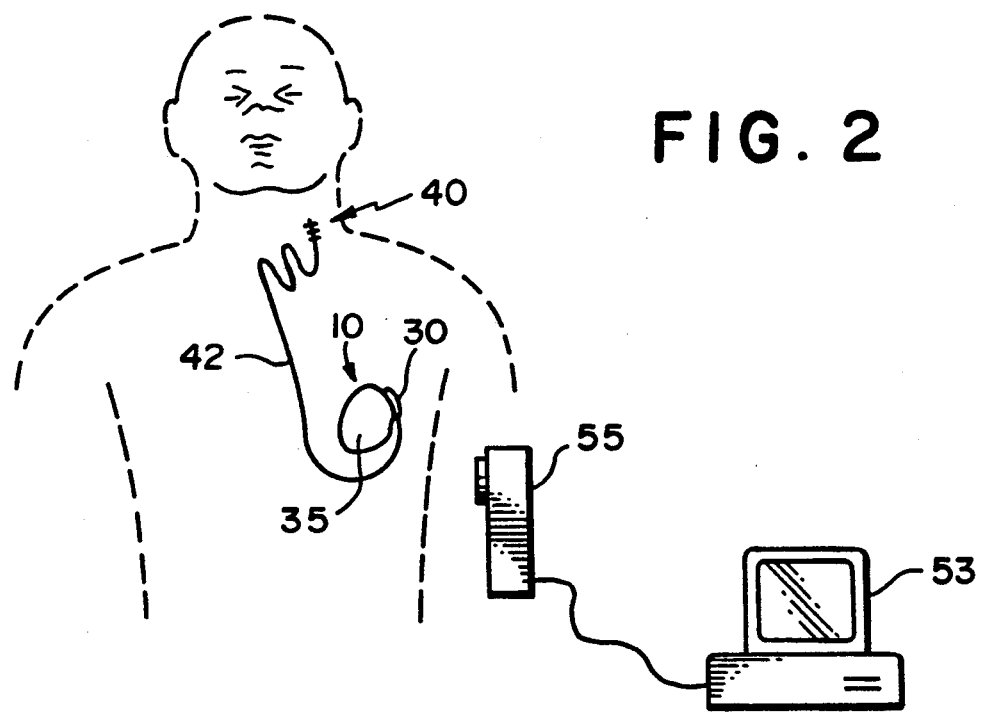
FIGS. 2 is a phantom view illustrating the relative positions of the implanted neurostimulator, nerve electrode array implanted on the vagus nerve, and associated electrical leads in the patient.

FIG. 1 is a simplified block diagram of an exemplary stimulus (pulse) generator of a neurostimulator to which the principles of the present invention may be applied. The device is used to treat and/or control epilepsy, for example, by application of appropriate modulating electrical signals to the patient's vagus nerve, as shown in FIG. 2. A detailed description of such a neurostimulator is contained in copending U.S. patent application Ser. No. 07/434,985, filed Nov. 10, 1989 in the names of Anthony Varicchio, et al.) assigned to the same assignee as the instant application, with modifications as will be described presently herein. For the moment, a brief description of the basic use, structure and operation of generator 10 of FIG. 1 will suffice.

Typically, pulse generator 10 is implemented to be implanted in the patient (e.g., in a pocket formed by the surgeon just below the skin in the chest as shown in FIG. 2), but the principles of the invention are not restricted to an implantable device and apply equally to a partly or primarily external system. The overall neurostimulator also includes an implantable stimulating electrode array 40 and electrical lead system 42 (FIG. 2) for applying the output signal of generator 10 to the selected nerve, such as the vagus nerve. For the implanted device, apparatus would also be employed external to the patient's body, including a computer 53 and wand 55 for telemetry of parameter programming to and monitoring signals from generator 10. The programmed stimulating output pulse sequence of the pulse generator is delivered to the nerve(s) to modulate the electrical activity thereof.

Generator 10 includes a battery (e.g., a single lithium thionyl chloride cell) 12 connected to a voltage regulator 15 which provides a clean, steady output voltage. The regulator supplies power to the various components, including logic and control section 17, which uses a microprocessor to control programmable functions of the device including current (and or voltage), frequency, pulse width, on-time and off-time of the output signal. This allows the output signal to be shaped to obtain the desired modulation of electrical activity of the nerve. Timing signals for the logic and control functions of the generator are provided by a crystal oscillator 20. A magnetically-actuated reed switch 27 may be incorporated in the electronics package to provide the capability for manual activation of the generator (e.g., by the patient, using an external magnet, not shown, placed immediately adjacent to the generator implant site). Built-in antenna 25 enables communication between the implanted pulse generator and the external electronics via the wand 55. Once the system is programmed, it maintains and operates at the programmed settings until reprogrammed (by the attending physician).

Logic and control section 17 controls an output circuit or section 22 which generates the output signal with the programmed parameters appropriate for treating epilepsy. The output section and its programmed output signal are coupled to an electrical connector 30 on the case or housing 35 of generator 10 and to lead assembly 42 connected to the stimulating electrode array 40 (FIG. 2). Housing 35 is hermetically sealed and composed of a material such as titanium which is biologically compatible with the fluids and tissue of the patient's body.

As shown in FIG. 2, nerve stimulating electrode array 40 is conductively connected to the distal end o insulated electrically conductive lead assembly 42 which is attached at its proximal end to connector 30 on the generator. Electrode array 40 may be a bipolar stimulating electrode of the type described in U.S. Pat. No. 4,573,481 issued Mar. 4, 1986 to Bullara. The electrode array is surgically implanted on the vagus nerve 45 in the patient's neck, and the lead assembly 42 is secured in a manner that allows it to flex with movement of the patient's chest and neck.

Figure 3:
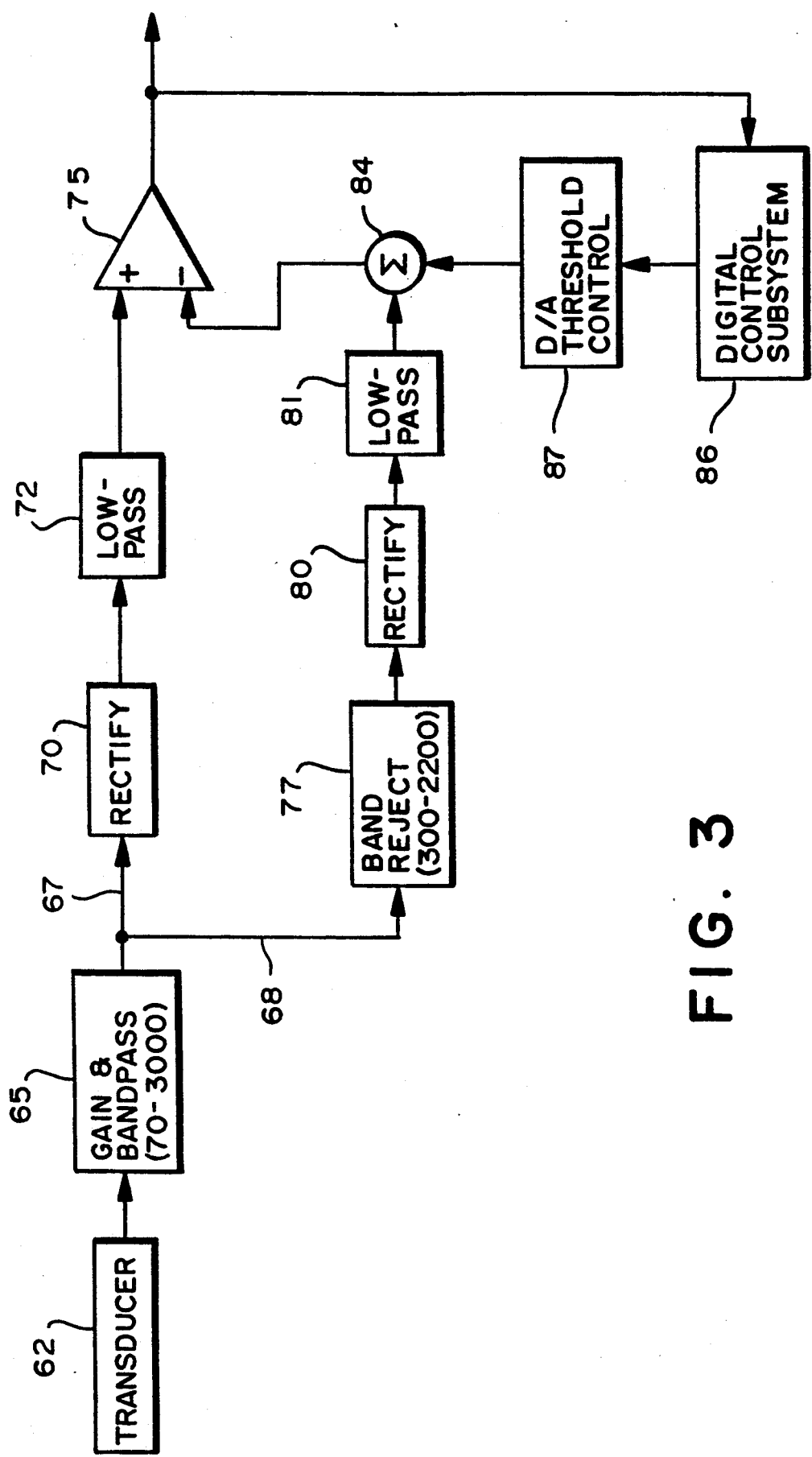
FIG. 3 is a block diagram of an exemplary embodiment of the invention employed in the neurostimulator of FIGS. 1 and 2.

It has been found that stimulation of the vagus nerve has a side effect of tending to produce an undesirable modulation of the patient's voice. According to the present invention, the neurostimulator includes apparatus for automatically and selectively suppressing or inhibiting the vagal stimulation while the patient is speaking. In the preferred embodiment, this apparatus comprises stimulation suppressor 60 (FIG. 1) which is mounted within the housing 35 of the stimulus generator 10. Preferably, a vibration transducer of the suppressor 60 is mounted on the interior surface of the generator housing, mechanically isolated from other internal components to permit free vibration of the transducer so that the suppressor will readily respond to vibrations arising when the patient speaks Referring to FIG. 3, the vibration transducer 62 of suppressor 60 is preferably a piezoelectric polymeric material marketed under the name Kynar ™, but any suitable material or device may be used which detects vibrations caused by speech-generated sound and converts them to a corresponding electrical signal.

The suppression system processes the speech-derived signal to provide programmable or adaptive sensitivity thereto. For purposes of initial discrimination between speech signals and other disturbances, the signal is subjected to bandpass filtering in the voice frequency band ranging from approximately 70 to 3,000 Hz. In the preferred embodiment, the output signal of the vibration transducer 62 is processed through an amplifier/filter 65 having a bandwidth wider than the speech signal, and is split into two signal paths 67 and 68. The signal in path 67 undergoes rectification in rectifier 70, and is then lowpass filtered via filter 72 in the frequency band of interest (time constant ranging from 0.3 to 3.0 seconds). The output of filter 72 is applied to one input of a comparator 75.

The signal in path 68 is attenuated in the normal frequency band of speech by a filter 77 having a frequency characteristic which rejects frequencies in the range from about 300 to about 2,220 Hz. The resulting signal is then rectified in rectifier 80 and lowpass filtered through filter 81 (same as filter 72). The output of filter 81 is combined in summing circuit 84 with a threshold value selected to provide a desired sensitivity to the signal of interest in the presence of ambient or background noise or other interference. The basic threshold value is programmed into the microprocessor memory in the digital control subsystem 86 of logic and control section 17 of the stimulus generator 10. This digital threshold value is converted to an analog value by digital-to-analog (D/A) converter 87 before being combined in sum/difference circuit 84 with the signal processed through path 68. The combination results in a signal which represents a threshold level exceeding the background noise in the vicinity of the patient and in the system. The cumulative threshold signal is applied as the second input to comparator 75.

When the first signal (the input from path 67, after processing) exceeds the cumulative threshold (the input from path 68, after processing, together with the threshold value from the microprocessor), it signifies detection of speech by the patient undergoing the neural stimulation. Accordingly, a "detect" signal is outputted from the comparator on line 90 and applied to the microprocessor, via digital control subsystem 86, to suppress stimulation of the vagus nerve by inhibiting the stimulating signal.

This basic speech detection system may be modified to avoid if not completely eliminate prolonged false detections, while facilitating rapid detection. Such a modification may be provided, for example, by progressively increasing the sensitivity of stimulation suppressor 60. In a preferred technique, the threshold level is initially programmed at a relatively small value so that the detection system is highly sensitive to vibrations indicative of sound, but not necessarily highly selective or capable of discriminating to a great extent between speech-generated sound and sounds deriving from other sources. If the processed first split signal voltage (output of path 67) crosses this threshold, the output of the comparator triggers suppression of the stimulation signal from the neurostimulator pulse generator. The suppression of stimulation may be selectively set to be brief, e.g., an interval of five seconds.

To decrease the sensitivity of the suppression system, the threshold is then increased (by prior programming of the microprocessor or by a predetermined added value with each "detect" output of the comparator). If the first split signal voltage exceeds this new threshold value, preferably measured within the time interval of the initial suppression, the stimulation signal remains inhibited. Suppression is continued for a period of time which is determined by balancing the patient's need for therapy against the desire to avoid objectionable voice modulation. This period of time is set by the attending physician, by appropriately programming the microprocessor in the logic and control section of the stimulus generator. Alternatively, the suppression may be aborted when the first split signal voltage fails to exceed a programmed lower threshold level, if that occurs before the end of the timer interval.

The suppression system may be implemented so that if the comparator fails to produce a "detect" signal output after an initial brief time interval that the first threshold is exceeded and a higher threshold level is established, the higher threshold level is maintained until the periodic testing of the detection subsystem demonstrates that the first split signal level has fallen well below the initial threshold level (i.e., an amount predetermined according to all relevant factors). To further preclude prolonged false detections of patient speech, the suppression system may be programmed to shut down (i.e., to discontinue further suppression) for a predetermined time interval after the physician-programmed period has timed out, or following an aborted detection.

Preferably, also, the sensing portion of the suppression system is implemented to provide a cumulative value representative of the number or extent of the time intervals during which stimulation is suppressed over the course of, for example, a twenty-four hour period. This information may then be utilized to reduce the amount of time of subsequent suppression cycles (i.e. to increase the duty cycle of the basic stimulation) if the summation exceeds a predetermined value for that period. Alternatively, the information may be used to increase the threshold level for speech detection.

When prolonged interruption of stimulation by the suppression system occurs, it tends to indicate that the sounds (vibrations in the system of the preferred embodiment) being detected may not be attributable to patient speech but instead are spurious signals or noise. These may include environmental sounds which are not easily discriminated from speech, such as snoring, wheezing or other respiratory problems of the patient. To avoid prolonged suppression of stimulation in these circumstances, the system preferably operates according to an algorithm which treats any prolonged suppression as though it is caused by false detections rather than patient speech. When a predetermined prolonged interval of suppression occurs, the suppression system is disabled. For example, a cumulative total of the intervals of suppression may be maintained by the system to automatically decrease the time interval during which suppression of stimulation is permitted in subsequent intervals, and at a predetermined total within a set time period, to prevent suppression altogether. Variations of such schemes, including adjustment of the stimulation or suppression duty cycle, can readily be developed with appropriate algorithms to serve the purpose of biasing the system against false detections and prolonged suppression.

It will be observed from the foregoing disclosure that the present invention provides automatic and selective suppression of stimulation of the vagus nerve while the patient is speaking, including the capability of automatically aborting the suppression whenever it has continued beyond a preprogrammed time interval. Because the basic function of the neurostimulator system is to modulate the electrical activity of the vagus nerve to relieve the incidence and/or length of epileptic seizures (or to alleviate some other disorder being treated), it is preferable to err on the side of stimulation during actual speech by the patient, despite accompanying undesirable voice modulation, than to allow prolonged intervals of non-stimulation.

Although a presently preferred embodiment and method of the invention have been described herein, it will be apparent to those skilled in the field of the invention from a consideration of the foregoing disclosure that variations and modifications of the disclosed embodiment and method may be made without departing from the spirit and scope of the invention. For example, the invention is not limited to use with implantable neurostimulators, but may be used effectively where part or substantially all of the neural stimulating apparatus is located external to the patient's body. Furthermore, the invention is not limited to the application of vagal stimulation for treatment of epileptic patients. Methods and apparatus for treating other disorders by vagal stimulation are described in copending U.S. patent applications assigned to the same assignee as the instant application, including Ser. Nos. 07/649,618 (filed Feb. 1, 1991), 07/660,404 (filed Feb. 22, 1991), and 07/695,216, 07/695,420, and 07/695,558 (each filed May 3, 1991). It is therefore intended that the invention shall be limited only to the extent required by the appended claims and the rules and principles of applicable law.

What is claimed is:

1. A medical device for stimulating the vagus nerve of a patient to modulate the electrical activity thereof as part of a prescribed therapy, comprising:
   signal generating means for generating a predetermined signal to stimulate the vagus nerve, and
   sensing means responsive to speech by the patient for automatically inhibiting said signal from stimulating the nerve.

2. The invention of claim 1, wherein
   said sensing means includes means for detecting speech by the patient.

3. The invention of claim 2, wherein
   said sensing means further includes means for removing the inhibition after a preset time interval regardless of continued detection of speech by the speech detecting means.

4. The invention of claim 2, wherein said sensing means further includes means for discriminating speech by the patient from other sounds to avoid false detection of speech.

5. The invention of claim 2, wherein
said sensing means further includes for varying the sensitivity of the speech detecting means to speech by the patient, to reduce the likelihood of false detection of speech.

6. The invention of claim 5, wherein
said sensing means further includes means for removing the inhibition after a preset time interval regardless of continued detection of speech by the speech detecting means.

7. The invention of claim 5, wherein
the sensitivity varying means includes means for progressively decreasing the sensitivity of the speech detecting means to speech-generated phenomena, to discriminate against similar phenomena generated by sources other than speech.

8. The invention of claim 5, wherein
the sensing means further includes
means for setting a threshold value of the speech detecting means representing a predetermined sensitivity to patient speech, and
the sensitivity varying means includes
means for progressively increasing the threshold value of the speech detecting means to speech-generated phenomena, with increasing intervals of inhibition.

9. The invention of claim 4, wherein
the speech detecting means includes a vibration sensor.

10. The invention of claim 9, wherein
the vibration sensor includes transducer means for converting detected vibrations to an electrical signal, and
the speech discriminating means includes bandpass filter means for processing the electrical signal derived from the detected vibrations while substantially rejecting signal frequencies outside the voice frequency band.

11. The invention of claim 1, wherein
said sensing means includes means for removing the inhibition after a preset time interval regardless of continued detection of speech by the speech detecting means.

12. The invention of claim 1, wherein
the sensing means includes
means for summing the time intervals of inhibition of the signal generated by said signal generating means during a predetermined period, and
means for reducing the time intervals of subsequent inhibitions when the sum of the time intervals of inhibition during said predetermined period exceeds a present value.

13. In conjunction with a medical device for stimulating the vagus nerve of a patient to modulate the electrical activity of the nerve as part of a prescribed therapy, the improvement comprising:
sensing means responsive to speaking by the patient for automatically suppressing the nerve stimulation.

14. The improvement of claim 13, wherein
said sensing means includes means for restoring the capability of the device to further stimulate the vagus nerve after a preset time interval regardless of continued speaking by the patient.

15. The improvement of claim 14, wherein
said sensing means further includes means for distinguishing speaking by the patient from other phenomena to avoid false responses.

16. The improvement of claim 13, wherein
said sensing means includes means for disabling the suppression despite continued speech by the patient.

17. The improvement of claim 13, wherein
said sensing means includes means for varying the sensitivity of the device to speech by the patient, after a predetermined time interval in which stimulation is suppressed.

18. A method of avoiding undesirable modulation of the voice of a patient as a consequence of stimulation of the patient's vagus nerve by a medical device to modulate the electrical activity of the nerve as part of a prescribed therapy, said method comprising:
sensing speech by the patient, and
responding to said sensing of speech by automatically suppressing the nerve stimulation.

19. The method of claim 18, further including
restoring the availability of stimulation after a preset time interval regardless of continued sensing of speech by the patient.

20. The method of claim 18, further including
distinguishing speech by the patient from other sounds to avoid suppression of stimulation in response to false detection of speech.

* * * * *